United States Patent [19]
Thurn et al.

[11] Patent Number: 6,004,558
[45] Date of Patent: Dec. 21, 1999

[54] METHODS FOR TREATING CANCER WITH LEGUME PLANT EXTRACTS

[75] Inventors: Michael Joseph Thurn; Li Jiu Huang, both of New South Wales, Australia

[73] Assignee: Novogen, Inc., Wilmington, Del.

[21] Appl. No.: 09/030,704

[22] Filed: Feb. 25, 1998

[51] Int. Cl.⁶ .............................. A61K 35/78; A61K 7/48
[52] U.S. Cl. ........................ 424/195.1; 424/45; 424/405; 424/422; 424/434; 424/451; 424/456; 424/465; 424/480; 424/489; 514/772.2; 514/938; 514/969
[58] Field of Search ................................ 424/195.1, 464, 424/439, 451, 456; 514/456, 969

[56] References Cited

U.S. PATENT DOCUMENTS

| | | | |
|---|---|---|---|
| 4,390,559 | 6/1983 | Zilliken | 426/545 |
| 5,141,746 | 8/1992 | Fleury et al. | 424/195.1 |
| 5,679,806 | 10/1997 | Zheng et al. | 549/403 |
| 5,830,887 | 11/1998 | Kelly | 514/182 |

FOREIGN PATENT DOCUMENTS

| | | |
|---|---|---|
| A-24813/97 | 12/1997 | Australia . |
| 0426998 A2 | 5/1991 | European Pat. Off. . |
| 61-246124A | 11/1986 | Japan . |
| 62-126186A | 6/1987 | Japan . |
| 01258669A | 10/1989 | Japan . |
| 02069165A | 3/1990 | Japan . |
| 03047049A | 2/1991 | Japan . |
| WO93/23069 | 11/1993 | WIPO . |
| WO94/23716 | 10/1994 | WIPO . |

OTHER PUBLICATIONS

Adlercreutz, H. et al., "Determination of Urinary Lignans and Phytoestrogen Metabolites, Potential Antiestrogens and Anticarcinogens, in Urine of Women on Various Habitual Diets," *J. Steroid Biochem,* vol. 25, No. 58, pp. 791–797 (1986).

Adlercreutz, Herman et al., "Dietary Phytoestrogens and Cancer In Vitro and In Vivo Studies," *J. Steroid Biochem Molec. Biol.,* vol. 41, No. 3–8 pp. 331–337 (1992).

Adlercreutz, Herman et al., "Dietary phyto–oestrogens and the menopause in Japan," *Lancet,* p. 1233 (1992).

Adlercreutz, H. et al., "Excretion of the Lignans Exterolactone and Enterodiol and of Equol in Omnivorous and Vegetarian Postmenopausal Women and in Women with Breast Cancer," *The Lancet,* pp. 1295–1299 (1982).

Adlercreutz, H. "Lignans and Phytoesrogens", *Front. gastrointest. Res.,* vol. 14, pp. 165–176 (1988).

Adlercreutz, Herman et al., "Urinary Excretion of Lignans and Isoflavonoids Phytoestrogens in Japanese Men and Women Consuming a Traditional Japanese Diet," *Am. J. Clin. Nutr.,* vol. 54, pp. 1093–1100 (1991).

Adlercreutz, Herman, "Western Diet and Western Diseases: Some Hormonal and Biochemical Mechanisms and Associations," *Scand. J. Clin. Lab. Invest, Suppl.,* vol. 201 pp. 3–23 (1990).

Anderson M.D., James et al., "Meta–Analysis of the Effects of Soy Protein Intake on Serum Lipids," *New Eng. J. Med.,* vol. 333, No. 5, pp. 276–282 (1995).

Barnes, Stephen et al., "Soybeans Inhibit Mammary Tumors in Models of Breast Cancer," *Mutagens and Carcinogens in the Diet,* pp. 239–253 (1990).

Bailey, E.T. et al., "Isoflavone Concentrations in the Leaves of the Species of the Genus Trifolium, Section Calycomorphum," Aust. J. Agric. Res., vol. 22, pp. 731–736 (1971).

Bannwart, Christoph et al., "Identification of the Isoflavonic Phytoestrogen daidzein in Human Urine," *Clinica Chimica Acta,* vol. 136, pp. 165–172 (1984).

Barrow, N.J. "Nutrient Potential and Capacity," *Aust. J. Agric. Res.,* vol. 17, pp. 849–861 (1966).

Barrow, N.J. et al., "Nutrient Potential and Capacity" (1966), Aust. J. Agric. Res. 18:55–62.

Beck, A.B., "The Oestrogenic Isoflavones of Subterranean Clover," *Aust. J. Agric. Res.* 15:223–30 (1964).

Beckham, N., "Menopause," *The Family Guide to Natural Therapies,* Greenhouse Publications, pp. 41–42, 50 (1988).

Beckham, Nancy, "Herbal Help to Avoid Menopause Symptoms," *Austrailian Wellbeing,* No. 29, pp. 74–76 (1988).

Beckham, Nancy, "Phyto–Oestrogens and Compounds that Affect Oestrogen Metabolism—Part I," *Aust. J. Med. Herbalism,* vol. 7, No. 1, pp. 11–16 (1995).

Beckham, Nancy, "Phyto–Oestrogens and Compounds that Affect Oestrogen Metabolism—Part II," *Aust. J. Med. Herbalism,* vol. 7, No. 2, pp. 27–33 (1995).

Bennetts, H.W. et al., "A Specific Breeding Problem of Sheep on Subterranean Clover Pastures in Western Australia," *The Australian Veterinary Journal,* vol. 22, pp. 2–12 (1946).

Beuker Velasse—Advertising Brochure—with English language translation.

Bombardelli, Ezio, "Technologies for the Processing of Medicinal Plants," in *The Medicinal Plant Industry,* Chapt. 7, pp. 85–98 (1991).

Bradbury, R.B. et al., "The Chemistry of Subterranean Clover. Part I. Isolation of Formononetin and Genistein," *J. Chem. Soc.,* pp. 3447–3449 (1951).

Bradbury, R.B. et al., "Estrogens and Related Substances in Plants," in *Vitamins and Hormones Advances in Research and Applications,* Harris, R.S. et al., eds., pp. 207–233 (1954).

(List continued on next page.)

*Primary Examiner*—Thurman K. Page
*Assistant Examiner*—Alysia Berman
*Attorney, Agent, or Firm*—Finnegan, Henderson, Farabow, Garrett & Dunner

[57] ABSTRACT

The present invention relates to the preparation of therapeutic compositions comprising extracts of leguminous plants from which the isoflavones genistein, daidzein, formononetin and biochanin and/or their glycosides have been removed. The invention also relates to therapeutic uses of such extracts in the treatment, prophylaxis, amelioration of, or defense against a variety of cancers.

6 Claims, No Drawings

OTHER PUBLICATIONS

Brandi, M.L., "Flavonoids: biochemical effects and therapeutic applications," *Bone and Mineral*, vol. 19 (Suppl.) S3–S14 (1992).

Braden, A.W.H. et al., "Comparison of Plasma Phyto–Oestrogen Levels in Sheep and Cattle After Feeding on Fresh Clover," *Aust. J. Agric. Res.*, vol. 22, pp. 663–670 (1971).

Braden, A.W.H. et al., "The Oestrogenic Activity and Metabolism of Certain Isoflavones in Sheep," *Aust. J. Agric. Res.*, vol. 18, pp. 335–348 (1967).

Circle, S. J. et al., "Processing Soy Flours, Protein Concentrates and Protein Isolates," *Soybeans: Chemistry and Technology*, vol. 1, pp. 294–338 (1972).

Coward, Lori et al., "Genistein, Daidzein, and Their β–Glycoside Conjugates: Antitumor Isoflavones in Soybean Foods from American and Asian Diets," *J. Agric. Food Chem.*, vol. 41, pp. 1961–1967 (1993).

Culbreth, David M.R., *A Manual of Materia Medica and Pharmacology*, pp. 19–22.

Davies, Lloyd H. et al., "Further Studies on Oestrogenic Activity in Strains of Subterranean Clover (*Trifolium Subterraneum* L.) In South–Western Australia," *Aust. J. Agric. Res.* (1965) 16:937–50.

Davis, Harold et al., "Extraction," *Bentley's Text–Book of Pharmaceuticals*, 6th ed., XVIII, pp. 272–273 (1956).

Düker, Eva–Maria et al., "Effects of Extracts from *Clinicifuga Racemosa* on Gonadotropin Release in Menopausal Women and Ovariectomized Rats," *Planta Med.*, vol. 57, pp. 420–424 (1991).

Eldridge, Arthur C., "Determination of Isoflavones in Soybean Flours, Protein Concentrates, and Isolates," *J. Agric. Food. Chem.*, vol. 30, pp. 353–355 (1982).

Eldridge, A.C., "High–performance Liquid chromatography separation of soybean iso–flavones and their glucosides," *J. Chrom.*, vol. 234 pp. 494–496 (1982).

Eldridge, Arthur C., et al. "Soybean Isoflavones: Effect of Environment and Variety on Composition," *J. Agric. Food Chem.*, vol. 31 pp. 394–396 (1983).

Farmakalidis, Efi et al., "Isolation of 6"–O–Acetylgenistin and 6"–O–Acetyldaidzin from Toasted Defatted Soyflakes," *J. Agric. Food Chem.*, vol. 33, pp. 385–389 (1985).

Farmakalidis et al., Semi–Preparative High–Performance Liquid Chromatographic Isolation Soybean Isoflavones, *J. Chrom.*, vol. 295, pp. 510–514 (1984).

Farnsworth, Norman R., et al. "Potential Value of Plants as Sources of New Antifertility Agents II," *J. Pharm. Sciences*, vol. 64, No. 5, pp. 717–754 (1975).

Francis., C.M. et al., "The Distribution of Oestrogenic Isoflavones in the Genus Trifolium," *Aust. J. Agric. Res.* 18:47–54 (1967).

Francis, C.M. et al., "Varietal Variation in the Isoflavone Content of Subterranean Clover: Its Estimation by a Microtechnique," *Aust. J. Agric. Res.* (1965) 16:557–64.

Gildersleeve, Rhonda R. et al., "Screening Rose Clover and Subterranean Clover Germplasm for Isoflavones," *Crop. Sci.*, vol. 31 pp. 1374–1376 (1991).

Gildersleeve, Rhonda R. et al., "Detection of Isoflavones in Seedling Subterranean Clover," *Crop Sci.*, vol. 31, pp. 889–892 (1991).

Gladstones, J.S., "Naturalized Subterranean Clover Strains in Western Australia: A Preliminary Agronomic Examination," *Aust. J. Agric. Res.*, vol. 18, pp. 713–731 (1967).

Herman, C. et al., "Soybean Phytoestrogen Intake and Cancer Risk," *American Institute of Nutrition*, pp. 7575–7705 (1995).

Holt, S., "Selected Bibliography of Scientific Studies on Genistein and Other Soya Isoflavones," Soya for Health: *The Definitive Medical Guide*, pp. 159–170 (1996).

Jenkins, David, J.A. et al., "Leguminous seeds in the dietary management of hyperlipidemia[1–3]," *Am. J. Clin. Nut.*, vol. 38, pp. 567–573 (1983).

Jones, Amanda E. et al., "Development and Application of a High–Performance Liquid Chromatographic Method for the Analysis of Phytoestrogens," *J. Sci. Food Agric.*, vol. 46, pp. 357–364 (1989).

Kaldas, Rami S. et al., "Reproductive and General Metabolic Effects of Phytoestrogens in Mammals," *Reproductive Toxicology Review*, vol. 3, No. 2, pp. 81–89 (1989).

Kitada, Yoshimi et al., "Determination of Isoflavones in soy bean by high–performance liquid chromatography with amperometric detection," *J. Chrom.*, vol. 366, pp. 403–406 (1986).

Knuckles, Benny E. et al., "Coumestrol Content of Fractions Obtained During Wet Processing of Alfalfa," *J. Agric. Food Chem.*, vol. 24, No. 6, pp. 1177–1180, (1976).

Kudou, Shigemitsu et al., "A New Isoflavone Glycoside in Soybean Seeds (*Glycine max* Merrill), Glycitein 7–O–β–D–(6"–O–Acetyl)–Glucopyranoside," *Agric. Biol. Chem.*, vol. 55, No. 3, pp. 859–860 (1991).

Kudou, Shigemitsu et al., "Malonyl Isoflavone Glycosides in Soybean Seeds (*Glycine max* Merrill)," *Agric. Biol. Chem.*, vol. 55, No. 9, pp. 2227–2233 (1991).

Linder, H.R., "Study of the Fate of Phyto–Oestrogens in the Sheep by Determination of Isoflavones and Coumestrol in the Plasma and Adipose Tissue," *Aust. J. Agric. Res.*, vol. 18, pp. 305–333 (1967).

Lock, Margaret, "Contested meanings of the menopause," *The Lancet*, vol. 337, pp. 1270–1272 (1991).

Martin, P.M. et al., "Phytoestrogen Interaction with Estrogen Receptors in Human Breast Cancer Cells," *Endocrinology*, vol. 193, No. 5, pp. 1860–1867 (1978).

Messina, Mark et al., "The Role of Soy Products in Reducing Risk of Cancer," *J. of National Cancer Institute*, vol. 83, No. 8, pp. 541–546 (1991).

Morris, P., "Identification and Accumulation of Isoflavonoids and Isoflavone Glucosides in Soybean Leaves and Hypocotyls in Resistance Responses to Phytophthora Megasperma f.sp. Glycinea," *Physiological and Molecular Plant Pathology*, 39 pp. 229–244 (1991).

Murphy, P.A., Phytoestrogen Content of Processed Soybean Products, *Food Technology*, pp. 60–64 (1982).

Murphy, P.A., "Separation of Genistin, Daidzin and Their Aglucones, and Coumesterol by Gradient High Performance Liquid Chromatography," *J. Chrom*, vol. 211, pp. 166–169 (1991).

Naim, M. et al., "A New Isoflavone from Soya Beans," *Phytochemistry*, vol. 12, pp. 169–170 (1973).

Naim, M. et al., "Soybean Isoflavones, Characterization, Determination, and Antifungal Activity," *J. Agr. Food Chem.*, vol. 22, No. 5, pp. 806–810 (1974).

Nash, A.M. et al., "Fractionation and Characterization of Alcohol Extractables Associated with Soybean Proteins. Nonprotein Components," *J. Agr. Food Chem.*, vol. 15, No. 1, pp. 102–108 (1967).

Ohta, Naokazu et al., "Isoflavonoid Constituents of Soybeans and Isolation of a New Acetyl Daidzin," *Agric. Biol. Chem.*, 43, vol. No. 7, pp. 1415–1419 (1979).

Okano, Koji et al., "Isolation of four Kinds of Isoflavon from Soya Bean," *Bron: Bull Agr. Chem. Soc. Japan.* 15, vol. 15, p. 110 (1939).

Okubo, Kazuyoshi et al., "Components Responsible for the Undesirable Taste of Soybean Seeds," *Biosci. Biotech. Biochem.,* vol. 56, No. I, pp. 99–103 (1992).

Pope, G.S., "The Importance of Pasture Plant Oestrogens in the Reproduction and Lactation of Grazing Animals," *Dairy Science Abstracts,* vol. 16, No. 5, pp. 333–356 (1954).

Price, K.R. et al., "Naturally Occurring Oestrogens in Foods—A Review," *Food Additives and Contaminants,* vol. 2, No. 2 pp. 73–106 (1985).

Reinli, Kathrin et al., "Phytoestrogen Content of Foods—A Compendium of Literature Values," *Nutrition and Cancer,* vol. 26, No. 2, pp. 123–148 (1996).

Rose, David P., "Dietary Fiber, Phytoestrogens, and Breast Cancer," *Nutrition,* vol. 8, No. 1 (1992).

Rossiter, R.C., "Physiological and Ecological Studies on the Oestrogenic Isoflavones in Subterranean Clover (*T. Subterraneum* L.)," *Aust. J. Agric. Res.,* Chapter III 18:23–37 (1967).

Rossiter, R.C., "Physiological and Ecological Studies on the Oestrogenic Isoflavones in Subterranean Clober (*T. Subterraneum* L.)," *Aust. J. Agric. Res.,* Chapter IV 18:39–46 (1967).

Seo, A. et al., "Improved High–Performance Liquid Chromatographic Analysis of Phenolic Acids and Isoflavonoids from Soybean Protein Products," *J. Agric. Food Chem.,* vol. 32, No. 3, pp. 530–533 (1983).

Setchell, K.D.R. et al., "High–Performance Liquid Chromatographic Analysis of Phytoestrogens in Soy Protein Preparations with Ultraviolet, Electrochemical and Thermospray Mass Spectrometric Detection," *J. Chrom.,* vol. 386 pp. 315–323 (1987).

Setchell, K.D.R. et al., "Mammalian Lignans and Phyto–oestrogens Recent Studies on their Formation, Metabolism and Biological Role in Health and Disease," in Role of the Gut Flora In Toxicity and Cancer, pp. 315–339 (1988).

Setchell, KDR et al., "Nonsteroidal estrogens of dietary origin: possible roles in hormone–dependent disease," *Am. J. Clin. Nut.,* vol. 40 pp. 569–578 (1984).

Shimoyamada, Makoto et al., "Saponin Composition in Developing Soybean Seed (*Glycine max* (L.) Merrill, cv. Mikuriyaao)," *Agric. Biol. Chem.,* vol. 55, No. 5, pp. 1403–1405 (1991).

Shutt, Donald A., "The Effects of Plant Oestrogens on Animal Reproduction," *Endeavour,* vol. 35, pp. 110–113 (1976).

Shutt, D.A. et al., "Free and Conjugated Isoflavones in the Plasma of Sheep Followed Ingestion of Oestrogenic Clover," *Aust. J. Agric. Res.,* vol. 18 pp. 647–655 (1967).

Shutt, D.A., "Interaction of Genistein With Oestradiol in the Reproductive Tract of the Ovariectomized Mouse," *J. Endrocrin.,* vol. 37, pp. 231–232 (1967).

Shutt, D.A. et al., "Quantitative Aspects of Phyto–Oestrogen Metabolism in Sheep Fed on Subterranean Clover (*Trifolium Subterraneum* Cultivar Clare) or Red Clover (*Trifolium Pratense*)," *Aust. J. Agric. Res.,* vol. 21, pp. 713–722 (1970).

Shutt, D.A. et al., "The Significance of Equol in Relation to the Oestrogenic Responses in Sheep Ingesting Clover With a High Formononetin Content," *Aust. J. Agric. Res.,* vol. 19, pp. 545–553 (1968).

Shutt, D.A. et al., "Steroid and Phyto–Oestrogen Binding to Sheep Uterine Receptors In Vitro," *J. Endocr.,* vol. 52, pp. 299–310 (1972).

Smith, G.R. et al., "Influence of Harvest Date, Cultivar, and Sample Storage Method on Concentration of Isoflavones in Subterranean Clover," *Crop Science,* vol. 26 (1986) pp. 1013–1016.

Trease, G.E. et al., "Pharmacognosy," $12^{th}$ Ed., pp. 242–260 (1983).

Verdeal, Kathey et al., "Naturally–Occurring Estrogens in Plant Foodstuffs—a Review," *J. Food Protect.,* vol. 42, No. 7, pp. 577–583 (1979).

Walter, E.D., "Genistin (an Isoflavone Glucoside) and its Aglucone, Genistein, from Soybeans," *J. Am. Chem. Soc.,* vol. 63, p. 3273 (1941).

Wang, G. et al., "A Simplified HPLC Method for Determination of Phytoestrogens in Soybean and Its Processed Products," *J. Agr. Food Chem.,* vol. 38, No. 1, pp. 185–190 (1990).

White, Edmund et al., "Extracta," *Pharmacopedia,* 2d ed. (1909).

Wilcox, G. et al., "Oestrogenic effects of plant foods in post–menopausal women," *British Med. J.,* vol. 301, pp. 905–906 (1990).

Wong, E., "Detection and Estimation of Oestrogenic Constituents in Red Clover," *J. Sci. Food Agric.,* vol. 13, pp. 304–308 (1962).

Wong, E., "The Oestrogenic Activity of Red Clover Isoflavones and Some of Their Degradation Products," *J. Endocrin.,* vol. 24, pp. 341–348 (1962).

"Estrogenic Activity in Plants," Brisbane Seminary (Summary of Talk by Nancy Beckham) (1985).

The Merck Index, Eighth Edition (1968).

"Phenolic Constituents," *Soybeans: Chemistry and Technology,* vol. 1, pp. 186–189 (1972).

"Solvent Treatment of Beans and Fractions," *Soybeans: Chemistry and Technology,* p. 149 (1972).

"Uterine Weight Changes and $^3$H–Uridine Uptake in Rats Treated with Phytoestrogens," *Can. J. Anim. Sci.,* vol. 60 pp. 531–534 (1980).

METHODS FOR TREATING CANCER WITH LEGUME PLANT EXTRACTS

TECHNICAL FIELD

This invention relates to compositions comprising extracts of isoflavone-containing plants from which the isoflavones genistein, daidzein, formononetin and biochanin have been removed. The invention also relates to therapeutic uses and the methods of treatment, particularly in the treatment of cancer.

BACKGROUND OF THE INVENTION

Isoflavones have been extensively described in the scientific and patent literature as possessing a range of biological activities including oestrogenic and anti-cancer effects.

Naturally occurring isoflavones are found in plants such as legumes. These include soy, chick peas, lentils, beans (broad, haricot, kidney, lima, navy, etc), grams (Bengal, horse and green) and clovers. Soy and clover contain the highest levels of isoflavones.

Principal oestrogenic and anti-cancer isoflavones are genistein, daidzein, formononetin, and biochanin. In plants these compounds occur principally in the glycoside form bound to sugars such as glucose. The formulae of these isoflavones are as follows:

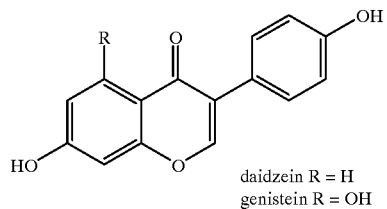

daidzein R = H
genistein R = OH the structure of biochanin is the same as for genistein but with a 4'-methoxy group, and similarly formononetin has the same structure as daidzein, but with a 4'-methoxy group. Isoflavone-containing plant extracts, such as from soy, are commercially available in some countries particularly as health supplements. Such extracts are specifically prepared for their isoflavone content, considerable effort being made to ensure the extracts contain maximum isoflavone content, the isoflavones being regarded as the biologically active species.

International Patent Application No. PCT/AU93/00230, incorporated herein by reference, describes isoflavone-containing extracts of a plant, such as legumes and clovers, and therapeutic uses for such isoflavone-containing extracts. The isoflavone extracts described therein specifically contain genistein, daidzein, formononetin and biochanin.

A recent clinical finding described in the *Medical Journal of Australia* (Stephens, F. O.. (1997) M. J. A., 167, 138–140) showed that an isoflavone extract prepared according to PCT/AU93/00230 produced major degenerative changes (including apoptosis) as shown by a prostatectomy specimen surgically removed from a patient with moderately high-grade adenocarcinoma. The patient received oral administration of the isoflavone-containing extract at a daily dose of 160 mg for seven days prior to surgery. The prostatectomy specimen showed a moderately high-grade adenocarcinoma with patchy microvaculation and prominent apoptosis, while no change was seen in normal prostate cells. The degenerative changes in the prostatectomy specimen, especially the apoptosis, were indicative of androgen deprivation and typical of a response to oestrogen therapy. This finding provided direct support for the oestrogen-like activity of the isoflavones genistein, daidzein, formononetin and biochanin exerting a positive therapeutic treatment in prostate cancer.

The inventors have surprisingly found that extracts of isoflavone-containing plants, such as soy or clover from which genistein, daidzein, formononetin and biochanin have been removed, have significant anti-cancer activity. This finding was contrary to all predictions, specifically given the absence of genistein, daidzein, formononetin and biochanin, regarded as the active anti-cancer agents.

SUMMARY OF THE INVENTION

In its broadest aspect this invention is concerned with a composition comprising an extract of isoflavone-containing plants such as soy or clover from which the isoflavones genistein, daidzein, formononetin and biochanin and/or their relevant glycosides (for convenience hereinafter referred to as (GDFB) have been removed.

In another aspect this invention is concerned with a composition which comprises a water/water-miscible alcohol extract of isoflavone-containing plants from which GDFB have been removed, which composition is optionally in association with one or more pharmaceutically acceptable carriers, excipients, auxiliaries, and/or diluents.

In accordance with another aspect of this invention there is provided a process for the production of a composition comprising an extract of isoflavone-containing plants such as soy or clover, which process comprises extracting the plants with a mixture of water and a water-miscible organic solvent, separating the water/water-miscible supernatant from residual undissolved plant material, and thereafter removing genistein, daidzein, formononetin and biochanin to form an extract, and optionally formulating the extract with one or more pharmaceutically acceptable carriers, excipients, auxiliaries, and/or diluents.

In a further aspect of this invention there is provided an extract of isoflavone-containing plants from which genistein, daidzein, formononetin and biochanin have been removed, for the manufacture of a medicament for the treatment, prophylaxis, amelioration or defence against cancer.

In accordance with another aspect of this invention there is provided a method for the treatment of prophylaxis, amelioration or defence against cancer which comprises administering to a subject in need of such a treatment an effective amount of a composition as described herein.

DETAILED DESCRIPTION OF THE INVENTION

In its broadest aspect this invention is concerned with a composition comprising an extract of isoflavone-containing plants, such as soy or clover from which the isoflavones genistein, daidzein, formononetin and biochanin (GDFB) have been removed. Such compositions may be in the form of pharmaceutical compositions, in association with one or more pharmaceutically acceptable carriers, excipients, auxiliaries and/or diluents. Compositions according to the invention have potent anti-cancer activity thereby allowing for the prophylaxis, amelioration, prevention and/or treatment of cancer.

Cancer is a major cause of death and of morbidity in the human population, particularly in the middle aged and elderly, but also across the whole human population including children. By way of example, breast cancer is a major cause of cancer in women, particularly after menopause (Bonett et al, (1992) *Eur. J. Cancer,* 1926). Prostate cancer is now the second most common cause of cancer death in men in the United States, where on average one in ten men may he expected to develop prostate cancer, with an average loss of life of nine years after cancer development.

Chemotherapy for the treatment of cancer is harsh, often generally being cytotoxic and affecting fast growing cells such as those of the intestinal region, and hair cells. Unpleasant side effects often include nausea, loss of taste, lethargy, hair loss, loss of libido, and the like. Anti-cancer therapeutic agents are generally costly and in some cases may only be administered by intravenous infusion.

The compositions of the present invention provide anti-cancer activity for the treatment, prophylaxis, amelioration and/or prevention of cancer, whilst overcoming one or more disadvantages of chemotherapeutic agents available for the treatment of cancer.

In accordance with an aspect of this invention there is provided a composition which comprises a water-miscible organic solvent extract of isoflavone-containing plant material, such as soy or clover from which the isoflavones genistein, daidzein, formononetin and biochanin have been removed.

The compositions of the present invention may be prepared from isoflavone-containing plants Indian liquorice (*Abrus precatorius*); various species of Acacia spp. including *A. aneura, A. cibaria, A. longifolia,* and *A. oswaldii*; ground nut (*Apio tuberosa*); ground pea (*Arachis hyogea*); milk vetch (*Astragalus edulis*); marama bean (*Bauhinia esculenta*); sword bean (*Cajanus cajan indicus*); jack bean (*Canavalia ensiformis*); sword bean (*Canavalia gladiata*); seaside sword bean (*Canavalia rosea*); various Cassia spp. including *C. floribunda, C. laevigata,* and *C. occidentalis*; carob bean (*Ceratonia siliqua*); chick pea (*Cicer arietinum*); yebnut (*Cordeauxia edulis*); various Crotalaria spp. including *C. laburnifolia,* and *C. pallida*; cluster bean (*Cyamopsis psoralioides*); tallow tree (*Detariaum senegalense*); word bean (*Entada scandens*); balu (*Erythrina edulis*); soya bean (*Clycine max*); inga (Ingaedulis); Polynesian chestnut (*Inocarpus fagifer*); hyacinth bean (*Lablab purpureus*); grass pea or Indian vetch (*Lathyrus sativus*); cyprus vetch (*Lathyrus ochrus*); lentil (*Lens culinaris*); jumping bean (*Leucaenal eucocephala*); various Lupinus spp. including *L. albus, L. luteus, L. angutstifolium, L. mutabilis* and *L. cosentinii*; ground bean (*Macotylma geocarpa*); horse gram (*Macrotyloma uniflorum*); alfalfa (*Medicago sativa*); velvet bean (*Mucuna pruriens*); yam beans (*Pachyrhyzuz erosus, P. tuberosus*); African locust bean (*Parkia clapprtoniana*); *Parkia speciosa*; oil bean tree (*Pentaclethra macrophylla*); various Phaesolus spp. including *P. acutifolius, P. vulgaris, P. luntus, P. coccineus, P. adenathus, P. angulris, P. aureus, P. calcaratus, P. mungo* and *P. polystachys*; garden pea (*Pisum sativum*); djenko bean (*Pithecolobium lobatum*); mesquite (various Prosopsis spp.); goa bean (*Psophocarpus scandens, P. tetragonolobus*); various Psoralea spp.; *Sesbania bispinosa*; yam bean (*Sphenostylis stenocarpa*); tamarind (*Tamarindus indica*); fenugreek (*Trigonella foenum-graecum*); vetches (varios Vivia spp. including *V. sativa, V. atropurpurea, V. ervilia* and *V. monantha*); broad bean (*Vicia faba*); black gram (*Vigna mungo*); various Vigna spp. including *V. radiala, V. aconitifolia, V. adanatha, V. angularus, V. tribolata, V. umbelata* and *V. unguiculata*; and earth pea (*Voandzeia subterranea*); and clovers (Trifolium) including red clover (*T. pratense*), subterranean clover (*T. subterranean*) white clover (*T. repens*), or any clover related species. An isoflavone-containing plant is any plant that contains one or more of daidzein, genistein, formononentin and biochanin, and/or glycosides and metabolites thereof. Soy and clover, such as red clover, are preferred isoflavone-containing plants.

Preferably tie compositions of the present invention comprise GDFB-free extracts of soy or clover. Plant material may be dried, and may be chopped or otherwise comminuted prior to an extract being prepared thereof.

As set forth above compositions according to the present invention may include one or more pharmaceutically acceptable carriers. The carriers are selected so as to be acceptable in the sense of being ingredients in the composition and must not be deleterious to the patient. The carriers may be solid or a liquid, or both, and may be formulated with the extract as a unit-dose, for example a tablet, which may contain from 0.5% to 59% by weight of the active compound or up to 100% by weight to the active compound. Compositions may be prepared by any of the well known techniques of pharmacy, (for example admixing the components, optionally including excipients, diluents (for example water) and auxiliaries as are well known in the pharmaceutical field.

The compositions according to the invention may include one or more active agents, such as vitamins (for example, Vitamin A, Vitamin B group, Vitamin C, Vitamin D, Vitamin E and Vitamin K), minerals (for example, magnesium, iron, zinc, calcium and manganese in the form of pharmaceutically acceptable salts), chemotherapy agents including anti-multi-drug resistant compounds (for example, alkylating agents, anti-metabolites, vinca alkaloids, antibiotic cytotoxics, hormonal antineoplastic agents, and synthetic cytotoxics), immune stimulators (for example, any interferon, interleukin, and growth hormones/growth factors), and anti-oxidants.

The compositions of the invention include those suitable for oral, rectal, optical, buccal (for example sublingual), parental (for example subcutaeous, intramuscular, intradermal and intravenous) and transdermal administration. The most suitable route in any given case will depend on the nature and severity of the condition being treated and the state of the patient.

Compositions suitable for oral administration may be presented in discrete units, such as capsules, cachets, lozenges, or tablets, each containing a predetermined amount of the extract; as a powder or granules; as a solution or a suspension in an aqueous or non-aqueous liquid; or as an oil-in-water or water-in-oil emulsion. Such compositions may be prepared by any suitable method of pharmacy which includes the step of bringing into association the active compound and one or more suitable carriers (which may contain one or more accessory ingredients as noted above). In general the compositions of the invention are prepared by uniformly and intimately admixing the extract with a liquid or finely divided solid carrier, or both, and then, if necessary, shaping the resulting mixture. For example, a tablet may be prepared by comprising or moulding a powder or granules containing the extract, optionally with one or more accessory ingredients. Compressed tables may be prepared by compressing in a suitable machine, the extracts in the form of a powder or granules optionally mixed with a binder, lubricant, inert diluents, and/or surface active/dispersing agent(s). Moulded tablets may be made by moulding, in a suitable machine, the powdered compound moistened with an inert liquid binder.

Suitable carriers may be fillers, such as sugars, for example lactose, saccharose, mannitol or sorbitol, cellulose preparations and/or calcium phosphates, for example tricalcium phosphate or calcium hydrogen phosphate, and also binders, such as starch pastes using, for example, corn, wheat, rice or potato starch, gelatin, tragacanth, methylceullose and/or polyvinylpyrrolidone, and, if desired, disintegrators, such as the above-mentioned starches, also carboxymethyl starch, cross linked polyvinyl pyrrolidone, agar or alginic acid or a salt thereof, such as sodium alginate. Excipients may be flow conditioners and lubricants, for example silicic acid, talc, stearic acid or salts thereof, such as magnesium or calcium stearate, and/or polyethylene glycol. Dragée cores are provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or dragée coatings, for example for identification purposes or to indicate different doses of active ingredients.

Other orally administrable pharmaceutical compositions are dry-filled capsules made, for example, of gelatin, and soft, sealed capsules made of gelatin and a plasticiser, such as glycerol or sorbitol. The dry-filled capsules may comprise the extracts in the form of granules, for example in admixture with fillers, such as lactose, binders, such as starches, and/or glicants, such as talc or magnesium stearate, and, where appropriate, stabilisers. In soft capsules, the extract is preferably dissolved or suspended in suitable liquids, such as fatty oils, paraffin oil or liquid polyethylene glycols, to which stabilisers may also be added.

Formulations suitable for buccal (sublingual) administration include lozenges comprising the extracts in a flavoured base, usually sucrose and acacia or tragacanth; and pastilles comprising the compound in an inert base such as gelatin and glycerin or sucrose and acacia.

Compositions of the present invention suitable for parenteral administration conveniently comprise sterile aqueous preparations of the extracts, which preparations are preferably isotonic with the blood of the intended recipient. These preparations are preferably admininistered intravenously, although administration may also be effected by means of subcutaneous, intramuscular, or intradermal injection. Suitable compositions include water soluble extracts and also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions comprising viscosity-increasing substances, for example sodium carboxymethylcellulose, sorbitol and/or dextran, and, where appropriate, also stabilisers. As an example compositions may conveniently be prepared by admixing the extracts with water or a glycine buffer and rendering the resulting solution sterile and isotonic with the blood. Injectable formulations according to the invention may contain from 0.1% to 60% w/v of the extract and may, for example, be administered at a rate of 0.1 ml/minute/kg.

Formulations suitable for rectal administration are preferably presented as unit dose suppositories. These may be prepared by admixing the extracts with one or more conventional solid carriers, for example cocoa butter, and then shaping the resulting mixture.

Compositions suitable for topical administration to the skin preferably take the form of an ointment, cream, lotion, paste, gel, spray, aerosol, or oil. Carriers which may be used include petroleum jelly, lanoline, polyethylene glycols, alcohols, and a combination of two or more thereof. The extract is generally present at a concentration of from 0.1% to 30% weight/weight, for example from 0.5% to 10% weight/weight.

Compositions suitable for transdermal administration may be presented as discrete patches adapted to remain in intimate contact with the epidermis of the recipient for a prolonged period of time. Such patches may contain the extracts in an optionally buffered aqueous solution.

Compositions suitable for transdermal administration may also be delivered by iontophoresis (see for example, *Pharmaceutical Research* 3 (6), 318 (1986)) and typically take the form of an optionally buffered aqueous solution of the extracts. Such compositions may, for example, contain citrate or bis/tris buffer (pH 6) or ethanol/water, with for example 0.05% to 30% w/w extract.

Compositions may be prepared in a manner, and in a form/amount as is conventionally practised. See for example, Goodman & Gillman, *The Pharmalogical Basis of Therapeutics* (7th Edition, 1985) and *Remington's Pharmaceutical Science*(Mack Publishing Company, 10th Edition), both of which are incorporated herein by reference. Compositions may contain, for example, from 0.1 mg to 2 g extract, such as 0.1 mg to 200 mg.

The extracts from which GDFB have been removed may be in the form of a powder, a slurry, in aqueous solution, particulate form, or dissolved in an organic solvent (such as methanol, ethanol, ethyacetate or dimethyl sulphoxide).

The extract from isoflavone-containing plant material, such as soy and clover is preferably a water/water-miscible organic solvent extract from which GDBF is specifically removed. The ratio of water to water-miscible organic solvent is generally in the order of 0.5% to 70% v/v water-miscible organic solvent, preferably from 1% to 30% water-miscible organic solvent. The water-miscible organic solvent is preferably a $C_{1-4}$ water-miscible organic solvent (such as methanol, ethanol, propanol, propylene glycol, erythrite, butanol, butanediol, acetonitrile, ethyleneglycol, glycidol, glycerol dihydroxyacetone or acetone). The extract in this regard is prepared by exposing the plant material to the water/water-miscible solvent mix. The exposure time in general terms is indirectly proportional to the temperature of the mixture. The temperature of the mix may range, for example, from an ambient temperature to boiling temperature. Exposure time may be between one hour to several weeks. One convenient extraction period is twenty four hours at 90° C. The extract is separated from undissolved plant material and the water-miscible organic solvent removed by distillation, rotary evaporation, or other standard procedures for solvent removal. The distillation residues containing water soluble and non-water soluble components are preferably extracted with non-water miscible organic solvent (such as petroleum ether, pentane, hexane, heptane, octane, benzene or toluene) and the aqueous phase discarded. The isoflavones genistein, daidzein, formononetin and biochanin may be removed at this stage to give the final extract, or alternatively the organic solvent may be removed to give a residue which may be dried and from which GDFB may be subsequently removed.

The isoflavones genistein, daidzein, formononetin and biochanin are removed from the extract to give a final plant extract as utilised herein by standard procedures. Examples include chromotagraphic techniques, such as preparative high performance liquid chromatography (IIPLC) using UV detection. Peaks of genistein, daidzein, formononetin and biochanin are identified by UV analysis and specifically removed. The eluate from which genistein, daidzein, formononetin and biochanin have been removed is then pooled and may be concentrated, (for example, by solvent removal and drying to give a power) with subsequent formulation into pharmaceutically acceptable compositions. Examples of chromatographic media include inorganic materials (such as porous silica, controlled poreglass hydroxy apatite, fluorapatite, aluminium oxide), composite materials (such as coated silica, coated polystyrene) and synthetic polymers (polyacrylamide, polymethacrylate, and polystyrene). The solvent phase for chromotographic separation may be an organic solvent such as methanol, ethanol, propanol, butanol, penatol, acetone, butanone, chloroform, dichloromethane, dichloroethane, dichlorobutane, ethylacetate, ether or dimethyl sulphoxide, which may be used to dissolve the extract. Other procedures for specifically removing isoflavones include differential extraction with organic solvents, based on the differing solubility of GDBF in certain organic solvents (see, for example, *Burdick and Jackson Solvent Guide*, Third Edition, Burdick and Jackson Laboratories, Muskegon, Mich., 1990).

In a further aspect of this invention there is provided a process for the production of a composition comprising an extract of isoflavone-containing plants such as soy or clover, which process comprises extracting the plants with a mixture of water and a water-miscible organic solvent, separating the water/water-miscible supernatant from residual undissolved plant material, and thereafter removing genistein, daidzein, formononetin and biochanin to form an extract, and optionally formulating the extract with one or more pharmaceutically acceptable carriers, excipients, auxiliaries, and/or diluents. Preferably the water soluble components are removed from the supernatant, such as by organic solvent extraction and discard of the aqueous phase.

What constitutes an effective amount of the compositions of the present invention will depend upon a number of factors, such as specific mode of administration, the cancer being treated, the condition of the patient and the judgement of the health care giver. Examples of dosages of extracts are about 0.1 mg to about 200 mg per day, such as in the order of 1.5 mg/kg (body weight)/day.

In cancer cells, the compositions of the present invention induce one or more effects of inhibition of cell proliferation, induction of cell differentiation, induction of apoptosis (programmed cell death), DNA fragmentation or cell cycle blocking. As a consequence, the compositions of the present invention have wide ranging activity against cancer cells and are accordingly effective in the treatment, prophylaxis, amelioration, defence against and/or prevention of cancers including benign prostatic hypertrophy, prostatic cancer, breast cancer, uterine cancer, leukaemia, ovarian cancer, endometrial cancer, cervical cancer, colon (large bowel) cancer, testicular cancer, Hodgkin's disease, lymphoma, rhabdo sarcoma, neuroblastoma, pancreatic cancer, lung cancer, brain tumour, skin cancer, stomach (gastric) cancer, oral cancer, liver cancer, laryngeal cancer, bladder cancer, thyroid cancer, and nasopharyngeal carcinoma. As the compositions of the present invention are free from side effects in all tests carried out to date, and given their natural product origin, they are especially suitable as prophylactics in the defence against cancer, In pre- and post-menopausal women, and in males, for example over the age of forty, the defence against highly prevalent cancers, such as breast cancer in women and prostate cancer in men, is highly advantageous from a number of perspectives. These include decreased mortality and morbidity, reduction in health care expenses, general patient well being and the like. The prevention or control of cancer, such as cancer of the prostate, breast, colon or leukaemia may be effected by daily administration of the compositions of the invention, such as by oral administration.

This invention will now be described with reference to the following non-limiting examples.

EXAMPLE 1

Red clover is harvested and dried by either sun-drying or applied heat. The material is optionally chaffed and extracted with a mixture of water-miscible organic solvent and water. Sixty percent ethanol in water is used. Extraction is carried out at 90° C. for twenty four hours. The supernatant is separated from undissolved plant material, and solvent removed by distillation. The residue comprising water, water soluble components and non-water soluble components is extracted with a non-water-miscible organic solvent (petroleum ether), followed by removal of the aqueous phase containing water soluble components. Removal of organic solvent by distillation (or drying under vacuum) gives a tar-like residue, which can be dried to give a powder, or which can be dissolved in organic solvent to give an isoflavone containing extract.

In the same manner as above, an isoflavone-containing extract is prepared from soy, hypocotyls and cotyledons.

EXAMPLE 2

Separation of primary isoflavones using chromatographic techniques

A red clover extract according to Example 1 is dissolved in either methanol, ethanol, propanol, butanol, pentanol, acetone, butanone, chloroform, dichloromethane, dichloroethane, dichlorobutane, ethyl acetate, ether or dimethyl sulphoxide. The supernatant is injected into a preparative HPLC system with UV detection. From The known retention times of GDBF these are removed and the remaining peaks combined to give isoflavone free extract. The solvent is removed by evaporation or distillation, and the final extract dissolved in a small amount of ethanol or dimethyl sulphoxide (DMSO), or dried to give a powder, optionally in association with one or more pharmaceutically acceptable carriers.

EXAMPLE 3

Method for extraction and removal of genistein, daidzein, formononetin and biochanin Fifty kilograms of a red clover according to Example 1 is placed in a 2000 L stainless steel drum. It is extracted with 1500 L acetone:hexane (3:7) mixed solvent with stirring at ambient temperature for between four to twenty hours.

The extract is dried under vacuum, (−40 KPa to −97 KPa) at 30° C. to 80° C.

The dried extract is placed in a 200 L stainless steel drum and washed with 100 L non-polar organic solvent (such as petroleum ether, pentane, hexane, heptane, octane, benzene or toluene) for four to ten times. The residue solid material is then produced after being dried under vaccum. Solvent was removed under vacuum (−40 KPa to −97 KPa) at 30° C. to 80° C.

The final product obtained at step 4 was dissolved in dimethyl sulphoxide (20 mg/ml to 100 mg/ml) for pharmacological testing.

EXAMPLE 4

Anti-cancer activity or isoflavone free cell extracts

Cancer cell lines are screened for anti-cancer activity. Cell lines are chosen to reflect most prevalent types of cancer in the human population, namely breast cancer, colon cancer, prostate cancer and leukaemia. The cell lines screened included leukaemia cell lines HL60 and K562, prostate cancer cell lines LNCaP (androgen receptor positive) and DU145 (androgen receptor negative), and colon cancer cell line HT29.

Anti-cancer activity was assessed by culturing cells in culture medium in the presence, or absence, of predetermined amounts of candidate anti-cancer agents and appropriate controls. Anti-cancer activity was measured by assessing inhibition of cell proliferation, cell cycle analysis, apoptosis, differentiation, DNA fragmentation and growth inhibition. Cell proliferation was measured by the incorporation of ($^3$II)-thymidine using the standard MTT assay (Marks et al, (1992) *Leukaemia Research,* 16:1165–1173). Cell cycle, apoptosis and DNA fragmentation are determined by flow cytometry (McCloskey et al (1994) *Clinical Immunology and Immunopathology,* 71:14–15).

Agents tested are genistein (A1), an isoflavone-containing extract of red clover (A2) according to Example 1, isoflavone free extracts of red clover and soy prepared according to Examples 2 (A3) and 3 (A4), and water soluble components of red clover prepared according to Example 1 (A5). Concentrations of agents tested are 0, 10, 20 and 40 $\mu$g/ml.

Controls which contained either only medium or medium and the carrier used for the agents, had no effect as expected. An anti-cancer effect is observed for A1, A2, A3 and A4, but not A5. A3 and A4 are much more potent than the other agents tested. For example, in one experiment, using the cell line LNCaP at 40 $\mu$g/ml agent (calculated on a weight/weight basis), A3 was between five and ten times more active than A1 and A2, showing 95% cell death and substantial cellular irregularities in the remaining cells indicative of an anti-cancer effect. This was a most surprising result as A3 and A4 were not expected to have anti-cancer activity. The same results were observed for the breast and leukaemia cell lines.

EXAMPLE 5

Treatment of a sixty two year old male diagnosed with prostate cancer

A sixty two year old healthy male was diagnosed with prostate cancer after two blood tests (two months apart) showed that his PSA (prostate specific antigent) level was elevated (46.5) and rising. The patient declined both radiotherapy and a surgery, so is placed on a composition according to Example 3 (160 mg/day) for a period of six months. The patient is monitored during this period and it is observed that the patient remained healthy, and that his PSA level had dropped to 4.5, this correlating with treatment of prostate cancer. The patient continues to take the isoflavone-free composition (40 mg/day).

Throughout this specification, unless the context requires otherwise, the word "comprise", or variations such as "comprises" or "comprising" or the term "includes" or variations thereof, will be understood to imply the inclusion of a stated element or integer or group of elements or integers but not the exclusion of any other element or integer or group of elements or integers. In this regard, in construing the claim scope, an embodiment where one or more features is added to any of claims is to be regarded as within the scope of the invention given that the essential features of the invention as claimed are included in such an embodiment.

Those skilled in the art will appreciate that the invention described herein is susceptible to variations and modifications other than those specifically described. It is to be understood that the invention includes all such variations and modifications which fall within its spirit and scope. The invention also includes all of the steps, features, compositions and compounds referred to or indicated in this specification, individually or collectively, and any and all combination any two or more of said steps or features.

References referred to herein are to be regarded as being incorporated be reference.

We claim:

1. A method for the treatment, prophylaxis, amelioration or defense against cancer which comprises administering to a subject in need of such a treatment an effective amount of a therapeutic composition comprising a legume plant extract from which the naturally-ocurring isoflavones genistein, daidzein formononetin and biochanin and their glycosides have been removed.

2. The method according to claim 1 wherein the subject in need of such treatment is suffering from breast cancer, prostate cancer, leukaemia, colon cancer, uterine cancer, ovarian cancer, endometrial cancer, cervical cancer, colon (large bowel) cancer, testicular cancer, Hodgkin's disease, lymphoma, rhabdo sarcoma, neuroblastoma, pancreatic cancer, lung cancer, brain tumour, skin cancer, stomach (gastric) cancer, oral cancer, liver cancer, laryngeal cancer, bladder cancer, thyroid cancer, or nasopharyngeal carcinoma.

3. The method according to claim 1 wherein the legume plant extract is a water/water-miscible alcohol extract, optionally in association with one or more pharmaceutically acceptable carriers, excipients, auxiliaries, and/or diluents.

4. The method according to claim 1 wherein said legume plant extract is an extract of soy or clover.

5. The method according to claim 4 wherein said extract is an extract of clover.

6. The method according to claim 1 wherein the clover is red clover.

* * * * *

UNITED STATES PATENT AND TRADEMARK OFFICE
CERTIFICATE OF CORRECTION

PATENT NO.: 6,004,558

DATED: December 21, 1999

INVENTOR(S): Michael Joseph Thurn; Li Jiu Huang

It is certified that an error appears in the above-identified patent and that said Letters Patent is hereby corrected as shown below:

In the Title Page, item [54], in line 2 of the Title, after "EXTRACTS", insert
--FROM WHICH NATURALLY-OCCURRING ISOFLAVONES HAVE BEEN REMOVED--.

Signed and Sealed this

Twenty-fourth Day of April, 2001

*Attest:*

NICHOLAS P. GODICI

*Attesting Officer*   *Acting Director of the United States Patent and Trademark Office*